US012251358B2

(12) United States Patent
Higgins

(10) Patent No.: US 12,251,358 B2
(45) Date of Patent: Mar. 18, 2025

(54) TRACKING OF CARDIAC RESUSCITATION PROCEDURE AND TRANSITIONS OF CARE

(71) Applicant: Rochester Regional Health, Rochester, NY (US)

(72) Inventor: Michael D. Higgins, Rochester, NY (US)

(73) Assignee: Rochester Regional Health, Rochester, NY (US)

( * ) Notice: Subject to any disclaimer, the term of this patent is extended or adjusted under 35 U.S.C. 154(b) by 666 days.

(21) Appl. No.: 17/508,666

(22) Filed: Oct. 22, 2021

(65) Prior Publication Data

US 2022/0040035 A1 Feb. 10, 2022

Related U.S. Application Data

(63) Continuation of application No. PCT/US2020/029828, filed on Apr. 24, 2020.
(Continued)

(51) Int. Cl.
*A61H 31/00* (2006.01)
*A61B 5/00* (2006.01)
(Continued)

(52) U.S. Cl.
CPC ......... *A61H 31/005* (2013.01); *A61B 5/4848* (2013.01); *A61B 5/7445* (2013.01);
(Continued)

(58) Field of Classification Search
CPC .... A61H 31/00–008; A61H 2201/5046; A61H 2201/5097; G16H 40/67;
(Continued)

(56) References Cited

U.S. PATENT DOCUMENTS

2010/0324612 A1 12/2010 Matos
2018/0092802 A1 4/2018 Giacometti et al.
(Continued)

FOREIGN PATENT DOCUMENTS

WO WO-2020/219891 A1 10/2020

OTHER PUBLICATIONS

International Search Report and Written Opinion for International Application No. PCT/US2020/029828 mailed Jul. 22, 2020.

*Primary Examiner* — Rachel T Sippel
(74) *Attorney, Agent, or Firm* — Foley Hoag LLP; Erik A. Huestis; Joshua S. Matloff

(57) ABSTRACT

Systems, methods, and computer program products for tracking of cardiac resuscitation procedures and transitions of care are disclosed. The method includes displaying on a first device one or more timers and a plurality of inputs, the plurality of inputs comprising patient health data, patient interventions, and medical events. The one or more timers, a feed of the medical events, and the patient interventions are displayed on a second device. One or more selections of the plurality of inputs are received from a user. A recommended cardiac resuscitation step is determined based on the user selections. The displaying on the second device is updated based on the one or more user selections and the recommendation. In various embodiments, a hand-off procedure may be implemented to transfer patient data, timers, event data, and/or user privileges from one healthcare professional to another.

7 Claims, 20 Drawing Sheets

Related U.S. Application Data

(60) Provisional application No. 62/838,570, filed on Apr. 25, 2019.

(51) Int. Cl.
 *G16H 40/67* (2018.01)
 *G16H 50/20* (2018.01)

(52) U.S. Cl.
 CPC ............. *G16H 40/67* (2018.01); *G16H 50/20* (2018.01); *A61B 2505/01* (2013.01); *A61H 2201/5046* (2013.01); *A61H 2201/5097* (2013.01)

(58) Field of Classification Search
 CPC .... G16H 50/20; A61B 5/4848; A61B 5/7445; A61B 2205/01
 See application file for complete search history.

(56) References Cited

U.S. PATENT DOCUMENTS

| | | | |
|---|---|---|---|
| 2018/0250519 A1* | 9/2018 | Chang | A61H 31/00 |
| 2020/0000679 A1* | 1/2020 | Oppenheimer | A61N 1/3993 |

\* cited by examiner

| IV Access | |
|---|---|
| Peripheral | |
| 14 Gauge | |
| 16 Gauge | |
| 18 Gauge | |
| 20 Gauge | |
| Other | |
| Central | |
| Triple Lumen | |
| Cordis | |
| Other | |
| IO | |
| Tibial | |
| Humeral | |
| Sternal | |
| Other | |

Fig. 3D

TRACKING OF CARDIAC RESUSCITATION PROCEDURE AND TRANSITIONS OF CARE

CROSS-REFERENCE TO RELATED APPLICATION

This application is a continuation of international application PCT/US2020/029828, filed Apr. 24, 2020, which claims the benefit of U.S. Provisional Application No. 62/838,570 filed Apr. 25, 2019, each of which is hereby incorporated by reference in its entirety.

BACKGROUND

Embodiments of the present disclosure generally relate to tracking of cardiac resuscitation procedures and transitions of care. In particular, the present disclosure describes an automated system for tracking and displaying events during the cardiac resuscitation process and providing recommended steps based on previously logged events.

BRIEF SUMMARY

According to embodiments of the present disclosure, systems for, methods for, and computer program products tracking a cardiac resuscitation procedure are provided. In various embodiments, the method includes displaying on a first device one or more timers and a plurality of inputs, the plurality of inputs comprising patient health data, patient interventions, and medical events. The one or more timers, a feed of the medical events, and the patient interventions are displayed on a second device. One or more selections of the plurality of inputs are received from a user. A recommended cardiac resuscitation step is determined based on the user selections. The displaying on the second device is updated based on the one or more user selections and the recommendation.

In various embodiments, a computer program product tracking a cardiac resuscitation procedure is provided in the form of a computer readable storage medium having program instructions embodied therewith. The program instructions are executable by a processor to cause the processor to perform a method where one or more timers and a plurality of inputs, the plurality of inputs comprising patient health data, patient interventions, and medical events are displayed on a first device. The one or more timers, a feed of the medical events, and the patient interventions are displayed on a second device. One or more selections of the plurality of inputs are received from a user. A recommended cardiac resuscitation step is determined based on the user selections. The displaying on the second device is updated based on the one or more user selections and the recommendation.

According to embodiments of the present disclosure, systems for, methods for, and computer program products for handing off a healthcare provider role during a transition of care are provided. In various embodiments, a first indication is received from a first user at a first device that a transition of care is to occur. The first device includes patient data, one or more timers, resuscitation event data, and a set of user privileges. A second indication is received from a second user at a second device that a transition of care is to occur. Patient data and the set of user privileges stored on the first device are transferred to the second device. The one or more timers are synchronized between the first device and the second device without the one or more timers stopping. In various embodiments, the patient data and the set of user privileges may be removed from the first device upon completion of the transfer.

In various embodiments, a computer program product for handing off a healthcare provider role during a transition of care is provided in the form of a computer readable storage medium having program instructions embodied therewith. The program instructions are executable by a processor to cause the processor to perform a method where a first indication is received from a first user at a first device that a transition of care is to occur. The first device includes patient data, one or more timers, resuscitation event data, and a set of user privileges. A second indication is received from a second user at a second device that a transition of care is to occur. Patient data, one or more timers, and the set of user privileges stored on the first device are transferred to the second device. The one or more timers are synchronized between the first device and the second device without the one or more timers stopping. In various embodiments, the patient data and the set of user privileges may be removed from the first device upon completion of the transfer.

BRIEF DESCRIPTION OF THE DRAWINGS

FIG. 1B illustrates a standard sheet for tracking cardiac resuscitation events.

FIGS. 3A-3H illustrate various components of the user interface for tracking cardiac resuscitation events according to embodiments of the present disclosure.

DETAILED DESCRIPTION

Figure 1A:
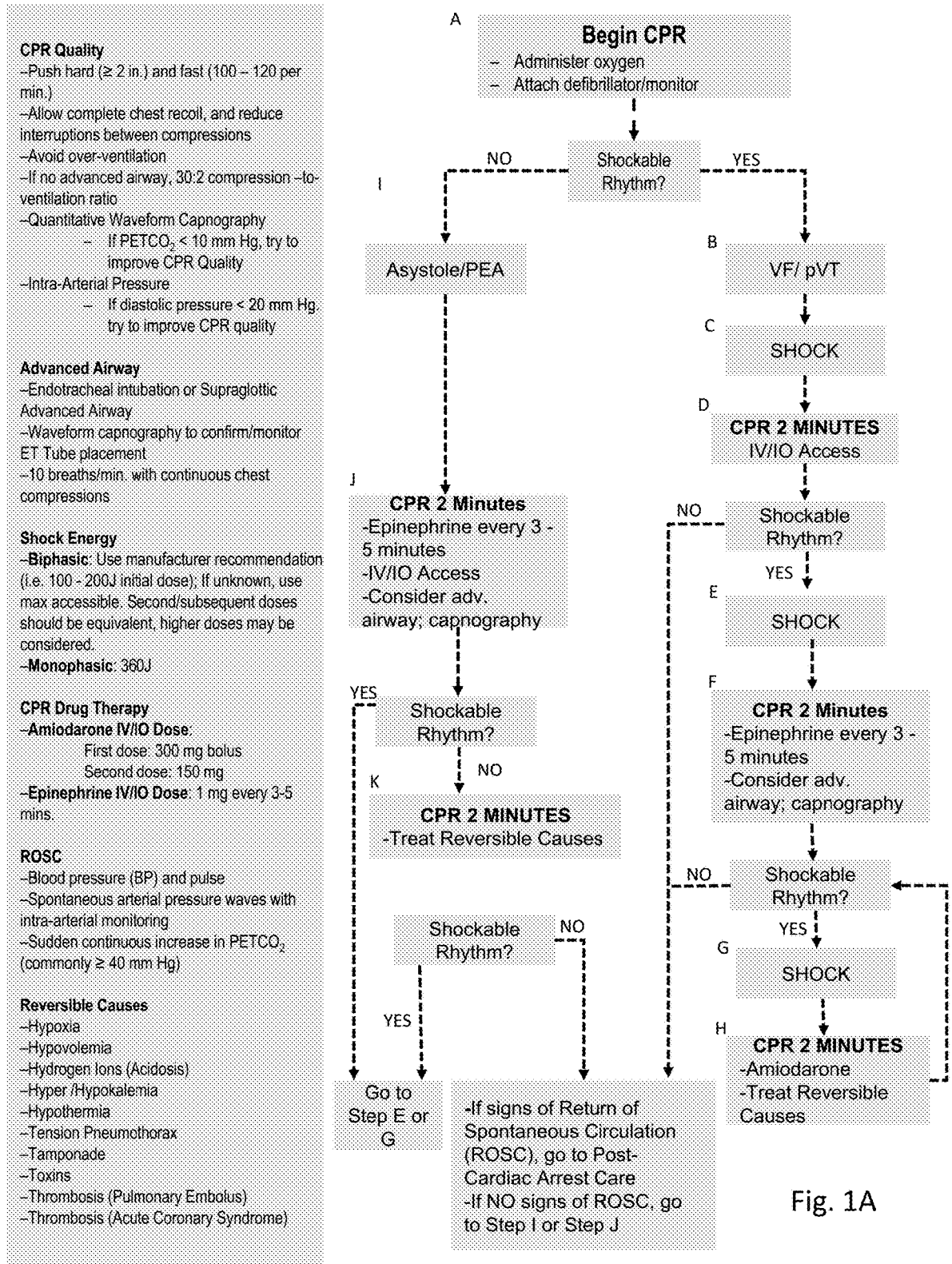
FIG. 1A illustrates a flowchart of a standard of care for treating cardiac arrest.

The resuscitation of a cardiac arrest poses a unique challenge in medicine. Very few pathologies outside of direct procedures require constant bedside attention and as significant departmental resources as a cardiac arrest. Because cardiac arrest resuscitation requires multiple nurses to carry out orders including a dedicated nurse who maintains records and monitors time sensitive events, a cardiac arrest resuscitation can be a logistical challenge for even a well-staffed department. Among the chaos and noise, a physician must coordinate these nurses as well as multiple technicians rotating CPR. The environment is typically loud and chaotic and communication between team members challenging.

Currently, the vast majority of cardiac arrests are handled with a stopwatch and paper. Events and timers are written down with their accompanying timestamp and an individual (e.g., a nurse) verbally communicates upcoming events to the physician. For example, the administration of epinephrine or the need to interrupt CPR for a pulse check both occur at fixed intervals in tandem with other dynamic events. Some practitioners and hospital systems may use digital stopwatches or smartphone applications designed to accompany cardiac arrest procedures and these applications contain a series of timers that keep track of the independent events. However, these applications often lack detailed logging systems and do not possess the ability to make corrections in real time requiring the nurse to fall back on rudimentary systems such as pen and paper and split their attention between these two sources of data entry. Additionally, these applications running on smart phones or tablets cannot be visualized by all members of the team and so the benefit of being able to anticipate, plan, and review the information is lost and reliance on verbal communication remains an ongoing challenge.

Another unique challenge with cardiac arrest is transition of care. Transitions of care in general are very error prone and are widely recognized as one of the areas of medicine where most medical error takes place. The transition of care of an active cardiac arrest undergoing resuscitation is particularly challenging because of the time sensitive nature of interventions (delays by even a few seconds can have detrimental outcomes), so time to review interventions done in the prehospital setting is very limited and often details are lost. No systems exists that allows all information of the ongoing arrest to be quickly and seamlessly transitioned from prehospital providers to hospital providers while maintaining all ongoing timers with accuracy. Moreover, no systems exist to allow this information to be transferred between hospital staff (e.g., physicians and/or nurses) in the event the physician and/or nurse is called to care for another emergency (e.g., another patient is rushed to the emergency room having a cardiac arrest).

This solution aims to use data that is recorded as standard-of-care by using an interface designed with the needs of the medical professional in mind. The data is used to create an external heads up display optimized for large format screens so that all members of the team can at a glance be updated on the current state of the resuscitation. It also contains systems by which ongoing resuscitations can be transferred between devices.

Accordingly, a need exists for a system and method to provide healthcare professionals with the ability to track cardiac resuscitation procedures effectively and display the information to a team of healthcare providers. Moreover, a need also exists for a system and method to provide healthcare professionals with the ability to quickly hand off lead responsibility to another healthcare professional in emergency situations. Such a solution would reduce medical error while increasing the accuracy and fidelity of information transitioned and allow it to be useful for the remainder of the resuscitation, not only posthumously.

In various embodiments, a software application may be used with a mobile logging device combined with an audio-visual heads-up display separate from the mobile logging device to act as a central coordination point by which alerts, actions, timers, and events are organized in a unique way to help maintain order and team synchrony. In various embodiments, the application may be configured to execute locally on mobile devices (e.g., a mobile phone or tablet). In various embodiments, a data model of all resuscitation events that could be recorded during a cardiac arrest was created and the ability to log these data points against an ongoing timer was implemented to thereby allow for dynamic tracking of all time-sensitive components of a resuscitation. In various embodiments, real time analysis of this database allows for audio visual alerts to be generated and timers with visual indicators to be displayed both on the local device as well as an external screen. The unique generation of an external screen provides a central means for all team members to be alert and aware of upcoming as well as previously occurring events, and allows new providers arriving to a resuscitation in progress to quickly become familiar with relevant events at a glance. This same display may show audio-visual alerts for critical actions that have been demonstrated to improve patient-centered outcomes and increase chance of restoring circulation. By generating a second external display the head nurse who is required to record all events can continue to focus on their primary task with an interface optimized for recording while a unique secondary interface is generated without additional effort on their part, to display information that previously needed to be relayed verbally. Verbal communication in these settings is particularly challenging and error prone as the environments are loud, chaotic, and high stress making them suboptimal to relay sensitive information verbally.

Transition of care is another area of medicine that has been demonstrated to be a great source of medical error, and the transition of care of a patient in cardiac arrest with ongoing resuscitation is by far one of the most challenging areas of hand off. Patients arriving from the prehospital setting are handed off by EMS verbally. Due to limitations in the field, EMS often does not have any printed records of their interventions and large amounts of detail is lost in the verbal handoff for the sake of brevity and limited resources. This application includes a digital handoff feature that allows EMS to use existing wireless peer to peer solutions to send data about an ongoing resuscitation with time synchronization across devices so no data is lost and verbal relay of information is only needed to augment or highlight the digital data.

The systems and methods described herein may reduce cognitive burden in a high stress scenario. Cardiac arrests are relatively uncommon and medical providers have varying degrees of experience and comfort. As a result, the quality of a resuscitation changes drastically depending on how many encounters are seen in a given time period. By comparing the logged data and the respective ongoing timers against known treatment protocols, recommendations are generated for which steps should be taken next.

In various embodiments, a standalone software application acts as the input interface for the person responsible for recording/logging the events of the resuscitation. In various embodiments, the application is written in any suitable coding language as is known in the art, such as, for example, Swift. In various embodiments, the systems and methods described herein are implemented on mobile devices for convenience of use in both the hospital and prehospital setting and the portability to bridge both of those environments. In various embodiments, all data is stored locally on the device using, for example, a Core Data model and database structure. Core Data is a data storage toolkit provided by iOS that is both robust and performant allowing for recurrent queries as the overall timer is refreshed multiple times per second. By using a local database, events can be modified or retimed (a common occurrence in cardiac arrests) and any dependent calculations based on these changes will be updated accordingly.

In various embodiments, a cloud server database may be used to store data, perform calculations, and/or provide recommendations as will be described in more detail below.

In various embodiments, the application may be in communication with an electronic health record EHR database.

In various embodiments, a secondary display allows for nonverbal communication of large amounts of information in an organized manner. In various embodiments, for the generation of the secondary display, two different technologies are implemented. In various embodiments, a screen mirroring feature may be used over either wireless connection or via a direct wired connection to an external display (e.g., LED monitor). In various embodiments, rather than providing 1:1 screen mirroring, a secondary interface is rendered, designed for large format displays (e.g., a standard 16:9 1080p television, though other aspect ratios and resolutions are supported). In various embodiments, the secondary display is not designed for touch input but rather for displaying relevant timers, a feed of recent events, total number of certain interventions (specific medications for example), as well as algorithmic recommendations of next steps based on prior events and current timer status. This information is periodically overridden with pop over alerts for time sensitive and critical interventions meant to gather the attention of all team members. The purpose of this interface is to reduce the need for ongoing verbally communication, which is the current standard way this information is transmitted. The interface also allows for real time review, inspection, analysis, and anticipation by all members of the team with the goal of streamlining the resuscitation process.

In various embodiments, another method that a secondary screen can be generated between two mobile devices may be implemented using an API, MultiPeerConnectivity. In various embodiments, the application may create peer-to-peer connections between other devices running the same application and render the secondary display using a series of network synchronization events to ultimately deliver the same functionality without the requirement of a dedicated screen or even a dedicated network. This method may be well-suited for more ad-hoc or rural scenarios where a dedicated display may not be available.

A vast majority of cardiac arrests happen in the prehospital setting. As a result, a significant portion of a resuscitation may happen before the patient actually arrives to the hospital. Transitioning care to the hospital team is particularly challenging and often only small amounts of information can be transitioned due to the ongoing needs of the resuscitation for the sake of brevity. By leveraging wireless communication technology (e.g., AirDrop), the relevant database entries can be encoded into a file format and transferred between devices quickly and seamlessly as a "hand-off." After transmission is complete, additional peer-to-peer network synchronization calls are made to ensure all timers maintain accuracy within a few milliseconds (depending on the latency of the wireless communication protocol) and the arrest picks up on the receiving device and all data including timestamps and totals are maintained resulting no loss of data fidelity or quality during transition of care. This allows providers to keep verbal handoff to only pertinent information.

Cardiac arrests contain many algorithmic components that are dictated by the American Heart Association Guidelines (e.g., by ACLS and/or PALS) in combination with other research papers. In an effort to offload cognitive burden, real time analysis of all events is performed and compared to known guidelines to suggest next steps that should be undertaken with regards to the resuscitation. These steps are combined with the ongoing time sensitive data to ensure recommendations only appear when appropriate time intervals have occurred. Additionally, warnings for interventions that need to be undertaken quickly, such as administration of an electrical defibrillation, are alerted on screen. Alerts for negative actions as well, such as long pauses in CPR, which have been shown even in short duration to cause significant decrease in cerebral blood flow, are included to help improve patient outcomes.

In various embodiments, the application is designed to function as a quality improvement and teaching tool. In various embodiments, simulation features may be included that allow time to be sped up or rewound for its use in a simulation setting. In various embodiments, report generation tools allow the collected data during the resuscitation to be exported into most electronic health records. These reports can optionally include quality improvement data and metrics designed to help future committees ensure maximum cardiac resuscitation quality.

FIG. 1A illustrates a flowchart 100 of a standard of care for treating cardiac arrest according to embodiments of the present disclosure. As shown in FIG. 1A, the flowchart for the standard of care for cardiac arrest of an adult patient includes several branches having many different steps to resuscitate a patient. At the first step, oxygen is administered and a defibrillator/monitor is attached to the patient. If the patient has a shockable rhythm, such as with ventricular fibrillation or permanent ventricular tachycardia, the patient is defibrillated. CPR is performed for 2 minutes and IV/IO access is established. If the patient has a shockable rhythm, the patient is defibrillated again. CPR is performed for another 2 minutes, epinephrine is administered every 3-5 minutes and advanced airway capnography is considered. If the patient has a shockable rhythm, the patient is defibrillated again. CPR is performed for another 2 minutes, amiodarone is administered, and reversible causes are treated. Reversible causes may include the H's and T's—hypoxia, hypovolemia, hydrogen ions (acidosis), hyper/hypokalemia, hypoglycemia, hypothermia, tension pneumothorax, tamponade, toxins, thrombosis (pulmonary embolus), thrombosis (acute coronary syndrome). If no shockable rhythm is present at any point, and signs of return of spontaneous circulation (ROSC) are present, the patient is given post-cardiac arrest care. If no shockable rhythm is present at any point, and no signs of ROSC are present, the second branch of the flowchart 100 is followed.

If the patient does not have a shockable rhythm, such as with asystole or pulseless electrical activity (PEA) patterns, then CPR is performed for 2 minutes, epinephrine is administered every 3-5 minutes, IV/IO access is established, and advanced airway capnography is considered. If a shockable rhythm is present, the patient is defibrillated, CPR is performed for 2 minutes, amiodarone is administered, and reversible causes are treated. The patient is then monitored for a shockable rhythm in a continuing cycle.

Cardiac resuscitation is generally dictated by the ACLS guidelines in adults (FIG. 1A) or the PALS guidelines in children. The PALS guidelines are similar to the ACLS guidelines except with a few variations. These guidelines may be used as a starting point for healthcare providers so that lower level medical providers can run a cardiac resuscitation. Physicians who practice critical care may deviate from these guidelines or use more invasive techniques at their disposal to try to improve outcomes based on more current research. One metric used is the chest compression fraction which is essentially a fraction of the amount of time chest compressions are occurring as the numerator with the total cardiac arrest time as the denominator. More current research has shown that keeping this fraction above 0.8 has improved circulation to the brain. In various embodiments, the system described herein may calculate in real time the chest compression fraction and display this fraction on a display with optional alerts/warnings when the value is dropping below the predetermined level (e.g., 0.8). Other deviations may include targeted medication administration based on certain hemodynamic properties of invasive monitors as opposed to the cyclical administration of medications. Another concept implemented by advanced resuscitation providers is careful monitoring of the duration of compression interruptions. Even a transient interruption in compressions results in a massive drop in perfusion of the brain that takes a long time to recover from so certain institutions have a dedicated person monitoring for interruptions and alerting the team when an interruption has reached a predetermined time threshold (e.g., 10 seconds). In various embodiments, transient interruption in compressions may be displayed. In various embodiments, a countdown timer and/or AV alert may be displayed if a long compression pause has occurred.

Figure 1B:
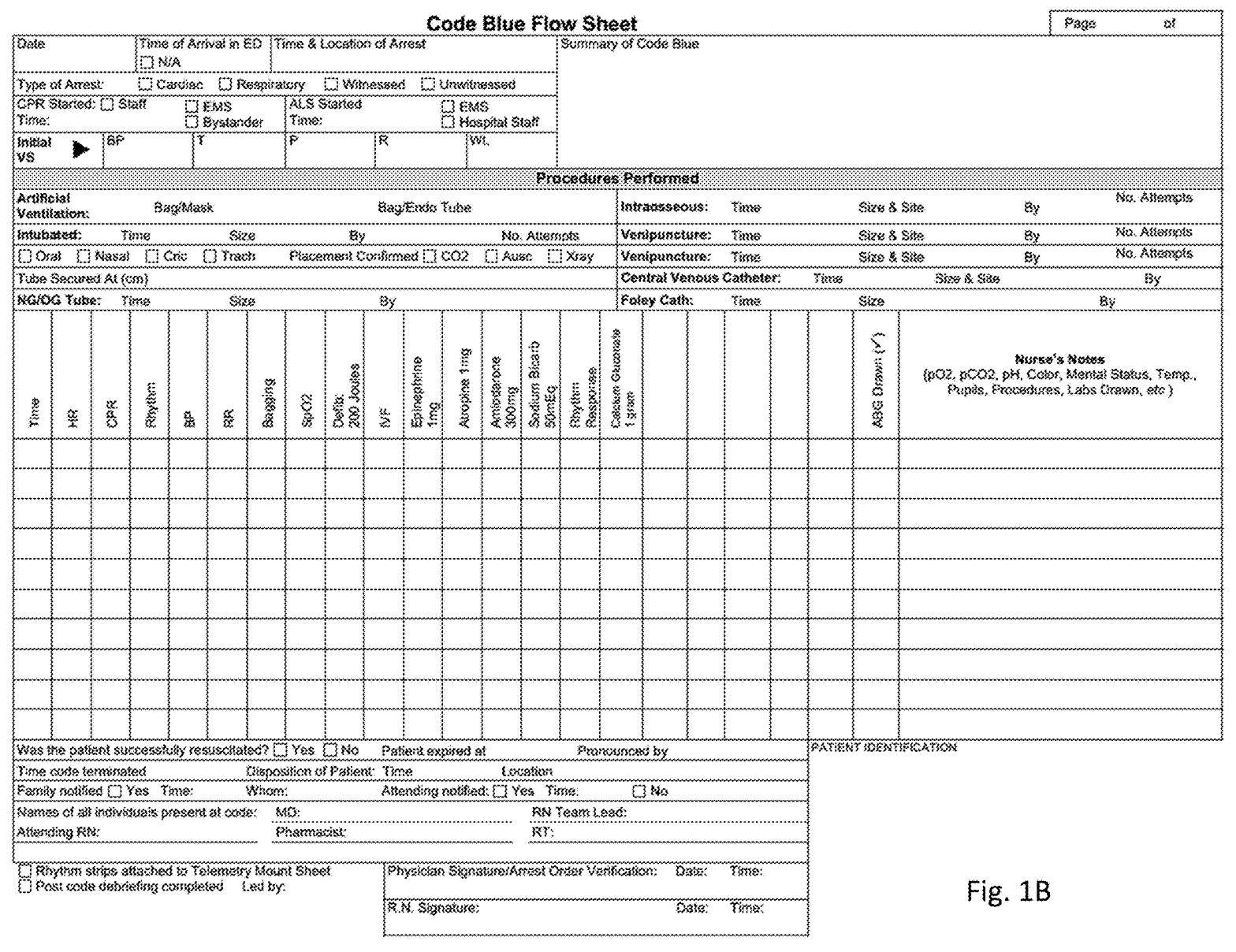

FIG. 1B illustrates a standard sheet for tracking cardiac resuscitation events, such as the event described in FIG. 1A. This sheet may be used to manually record resuscitation events on paper.

Figure 2:
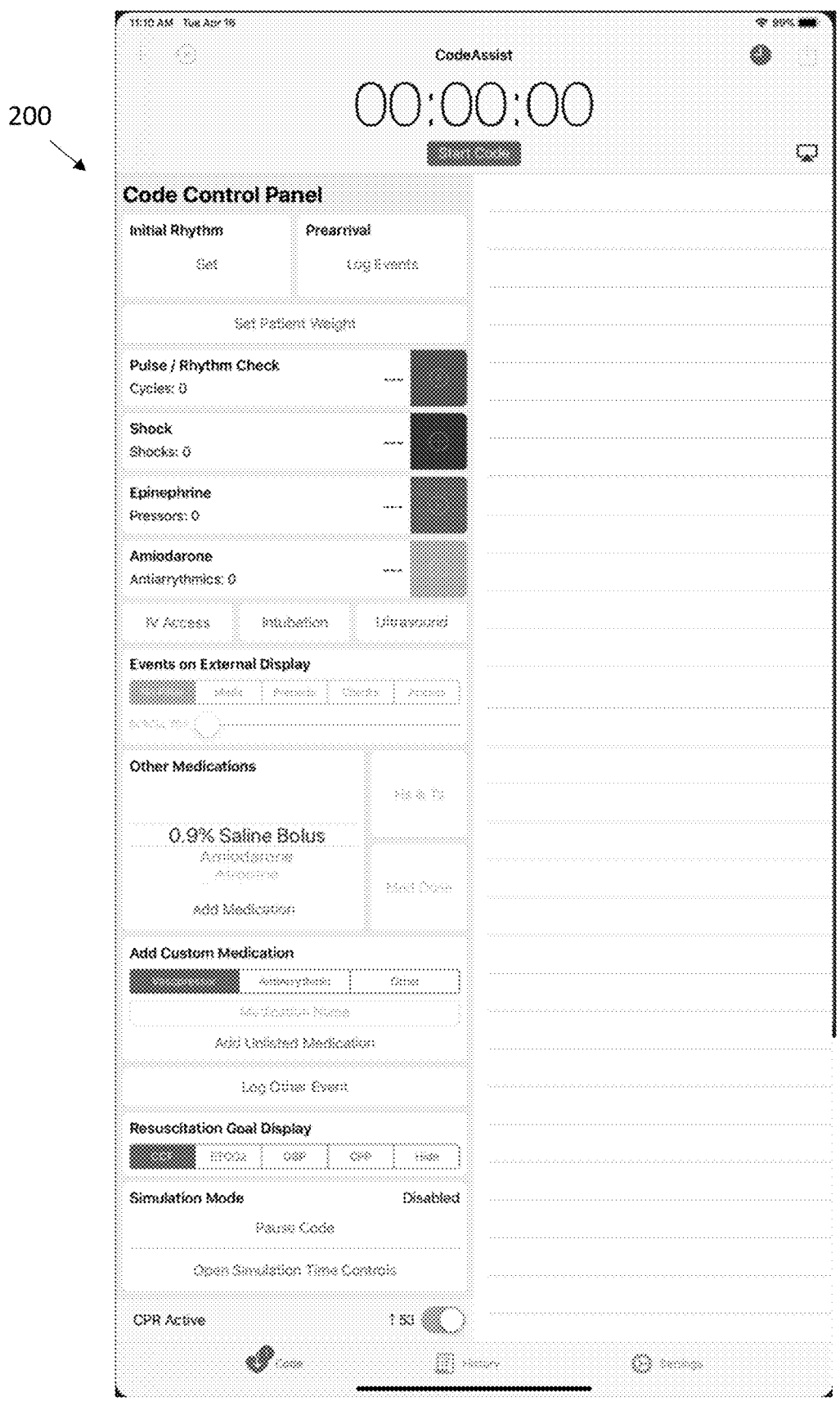
FIG. 2 illustrates a user interface for tracking cardiac resuscitation events according to embodiments of the present disclosure.

FIG. 2 illustrates a user interface 200 for tracking cardiac resuscitation events according to embodiments of the present disclosure. In various embodiments, the user interface 200 may include any suitable number of logging modules in the control panel, such as, for example, a number of cycles of a pulse/rhythm check, a number of shocks, a number of epinephrine administrations, a number of anti-arrhythmic administrations. In various embodiments, the user interface 200 may include an option panel for an external display. In various embodiments, the user interface may include a medication list, a custom medication tool, a resuscitation goal display, simulation mode controls, and/or a CPR active toggle switch.

In various embodiments, the most common and recurring events may be assigned UI elements. For example, total counts, timers, progress bar, etc. may be prominently displayed on the second display. In various embodiments, lesser accessed events may be displayed differently than the most common events. For example, defibrillation may include a voltage adjustment interface, airway logging and/or IV access may include a unique interface for the required parameters/variables, etc.

Figure 3A:
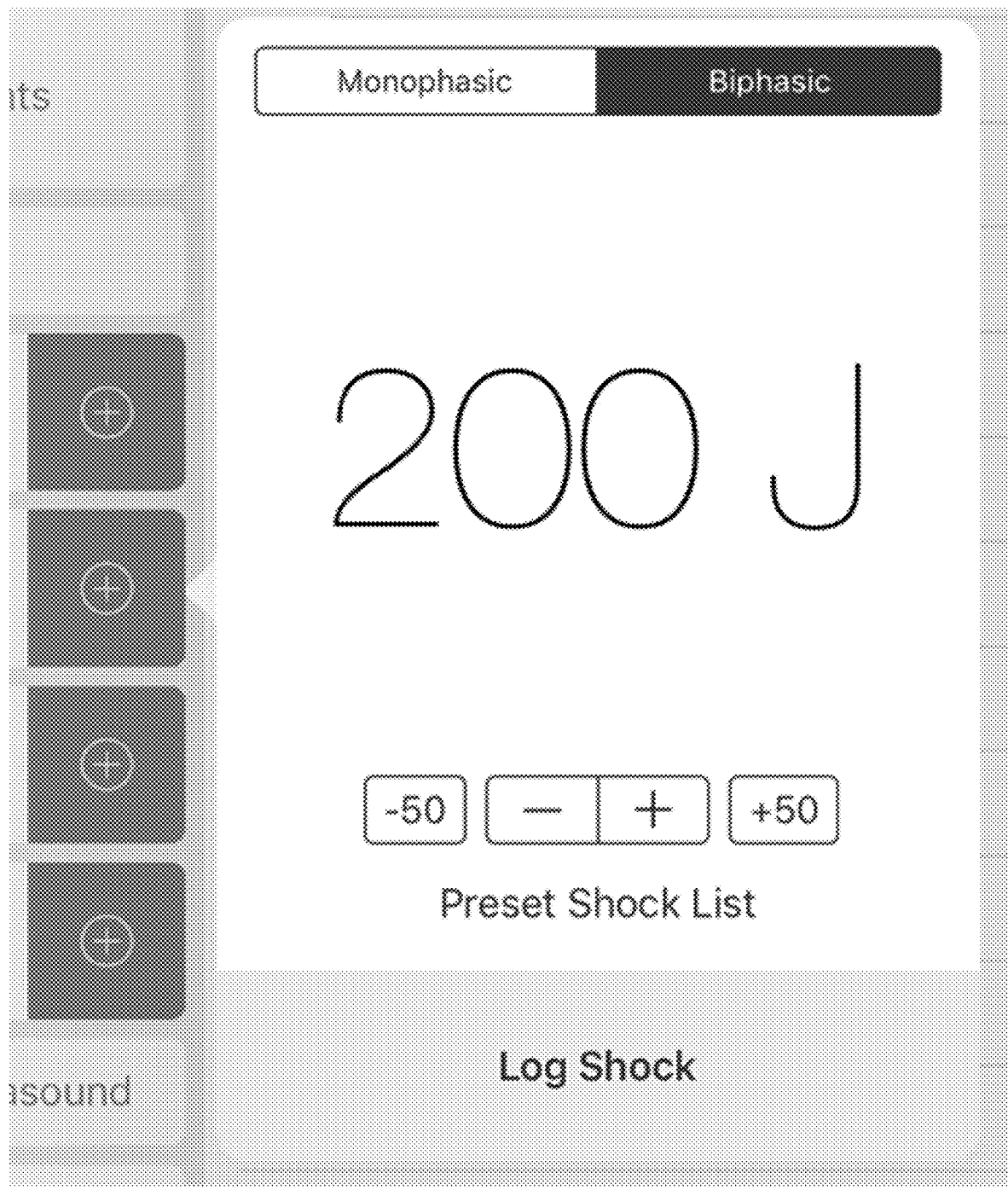
Figure 3B:
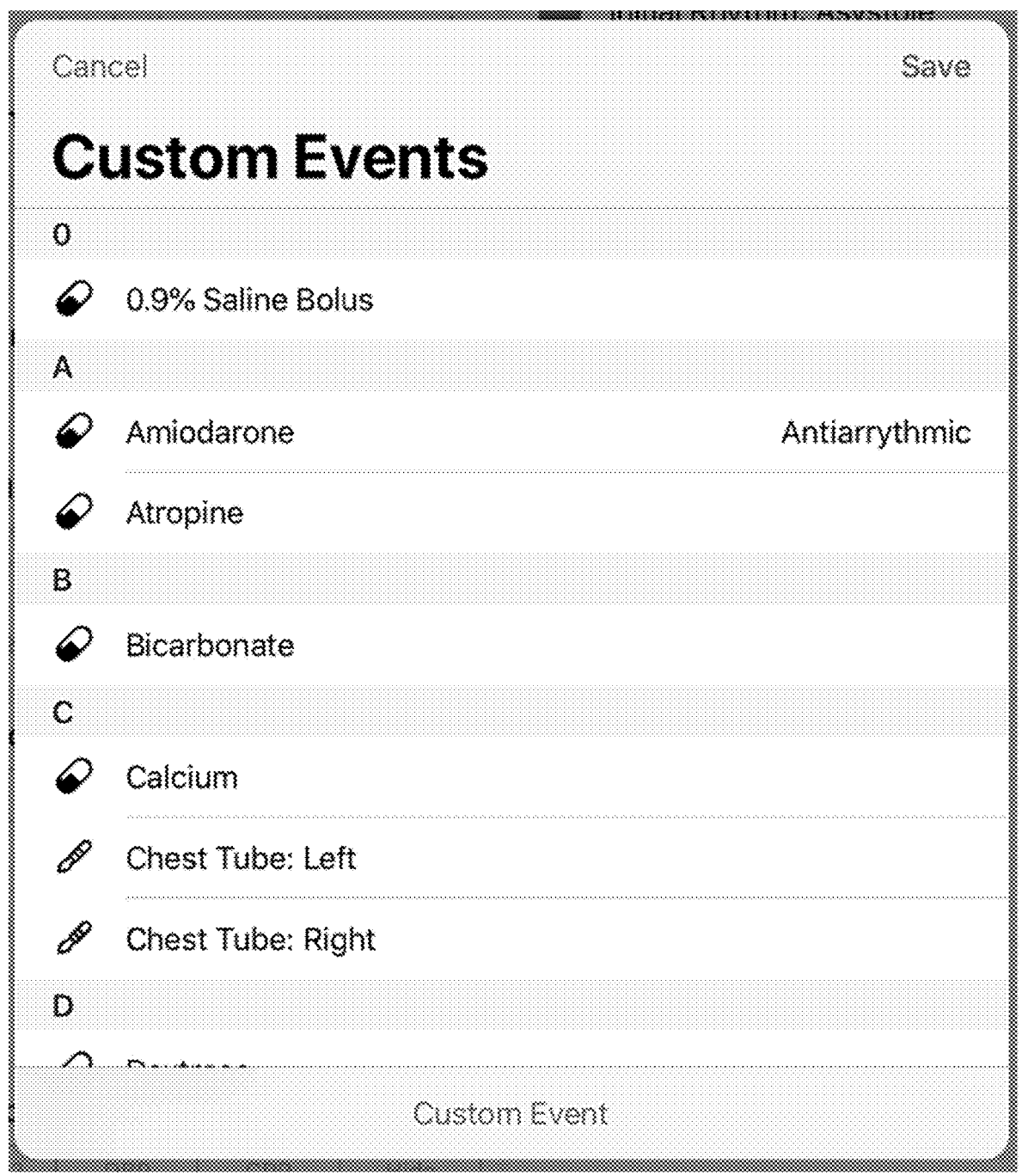
Figure 3C:
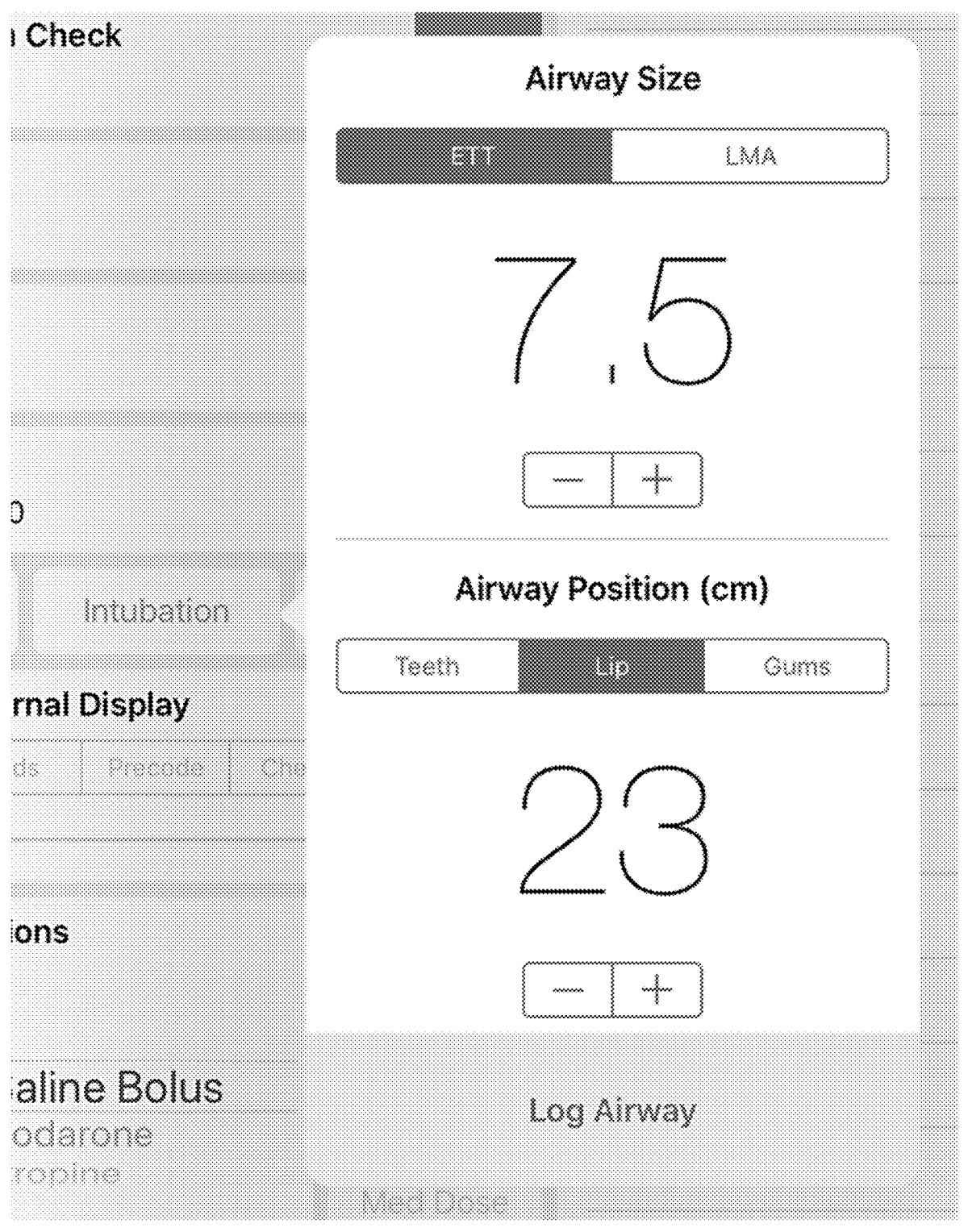
Figure 3E:
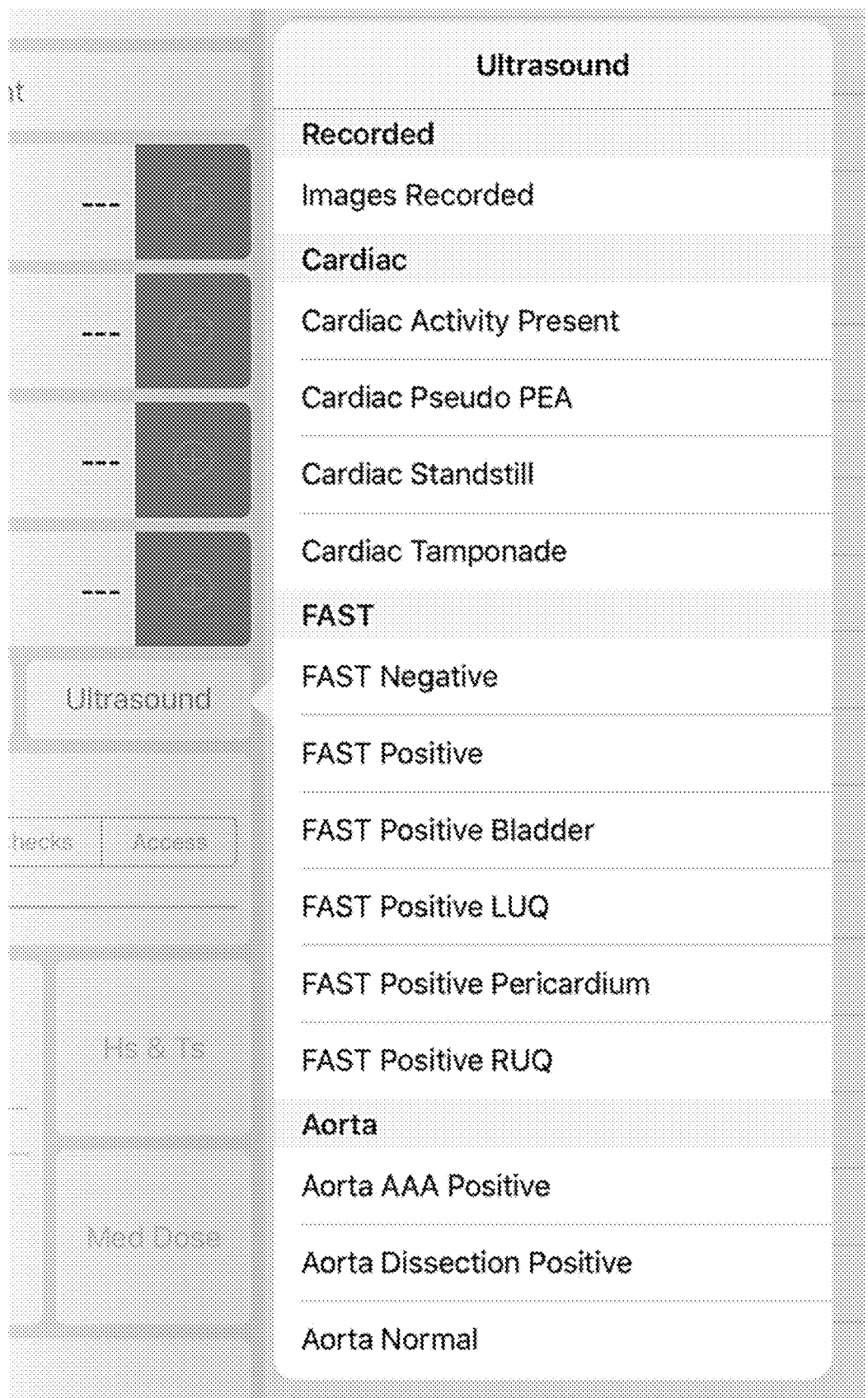
Figure 3F:
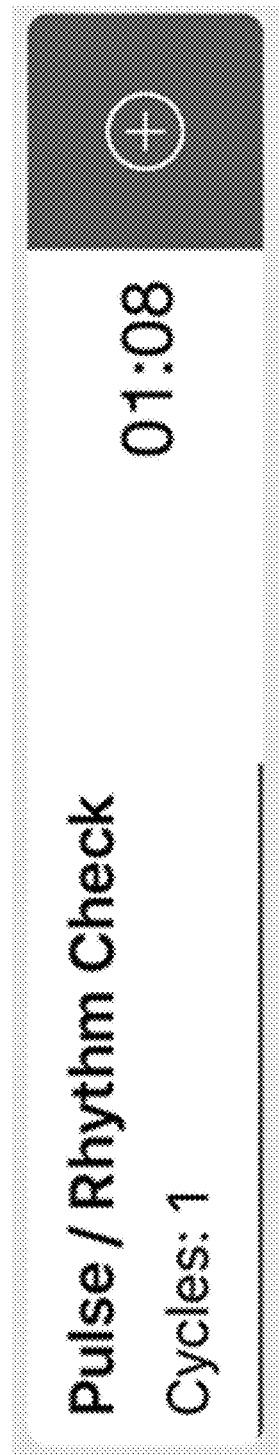

FIGS. 3A-3G illustrate various components of the user interface for tracking cardiac resuscitation events according to embodiments of the present disclosure. As shown in FIG. 3A, defibrillation information may be logged and may include the ability to adjust phase of shock and voltage that is logged. As shown in FIG. 3B, custom events may be assigned selected from a database of common events as well as a custom event writer so that a healthcare provider may enter custom event labels. As shown in FIG. 3C, airway information may be logged including, for example, airway size and position. As shown in FIG. 3D, IV information may be logged including, for example, location, size, and/or laterality. As shown in FIG. 3E, ultrasound information may be logged including, for example, common ultrasound findings displayed for quick access. As shown in FIG. 3F, a Quick Add View may be used for any number (e.g., four) of the most common elements of the arrest. In various embodiments, the quick add view may include a progress bar, total count, timer, and/or swipe to quick delete action. In various embodiments, when alternative medications are available in the same class, a long press on the add button displays these alternatives. In various embodiments, when the system determines a recommendation, an add button may be highlighted (e.g., begin to pulse) as a visual indicator to the healthcare provider logging the events.

Figure 3G:
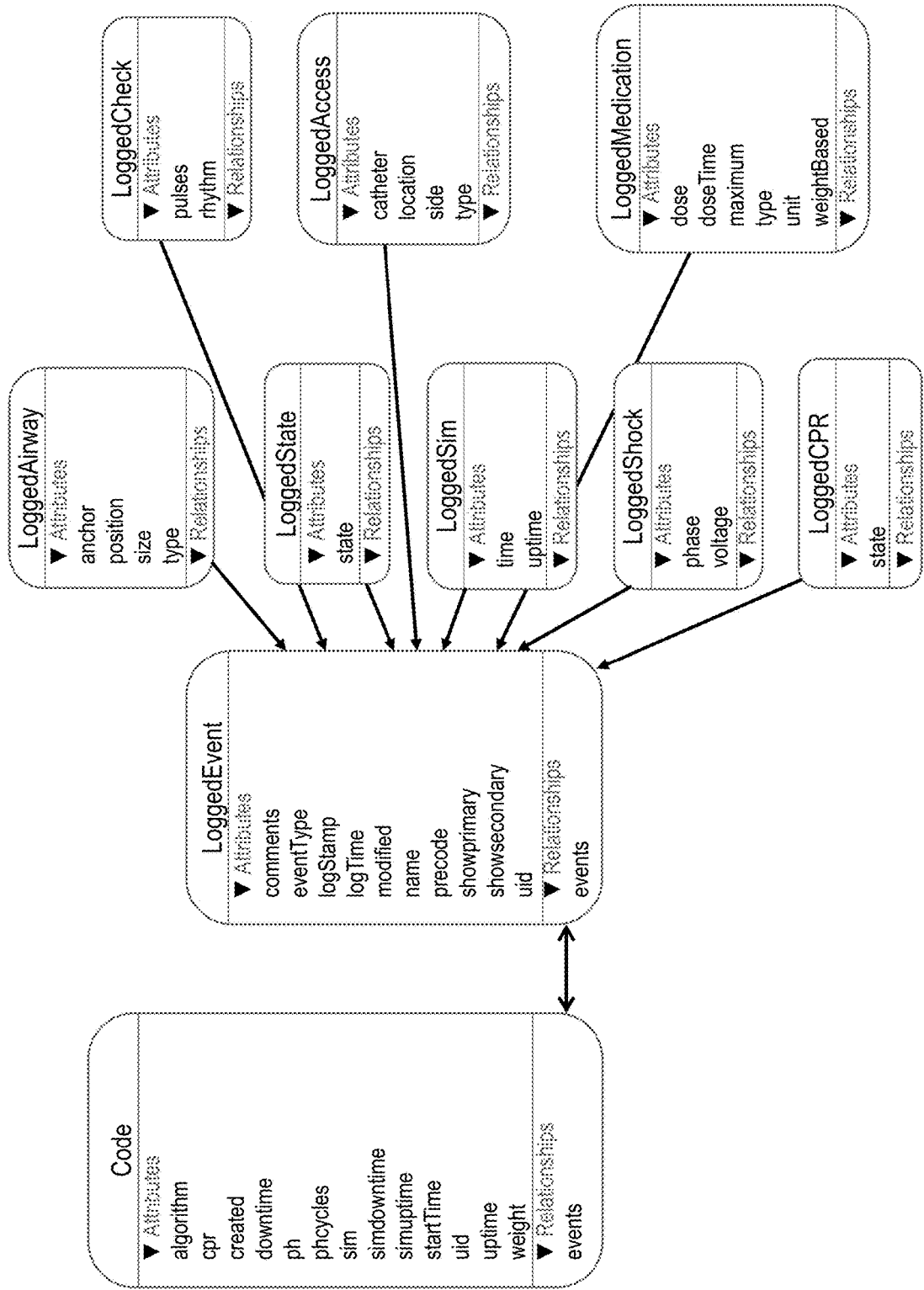
Figure 3H:
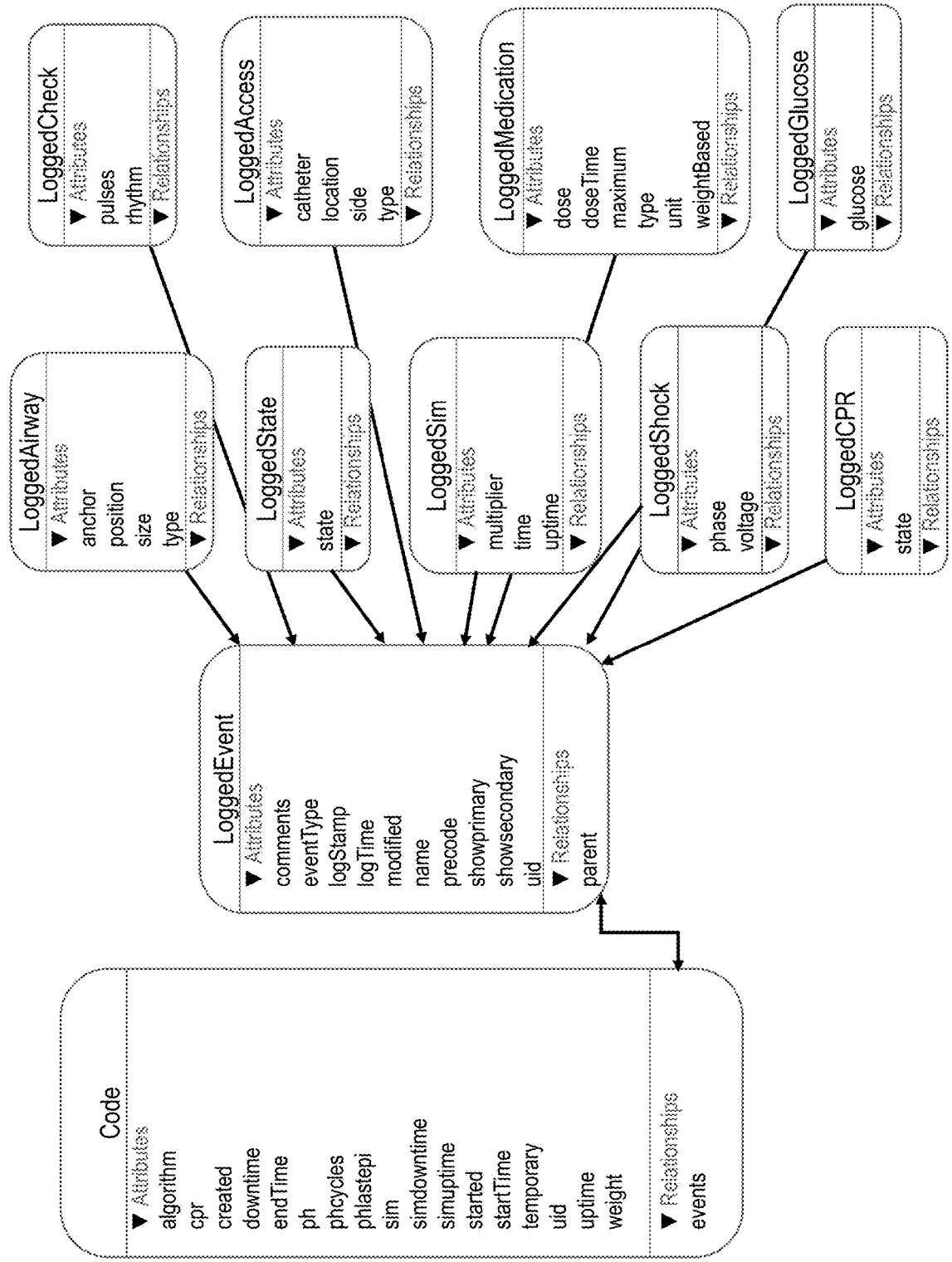

FIG. 3G and FIG. 3H show exemplary data models of the present disclosure. In various embodiments, events that can be logged may include any of the following: CPR start/stop, Pulse/rhythm checks, Medication administrations, Procedures, Airway access, IV access, IO access, Ultrasound, Point of care testing, and/or Defibrillation. In various embodiments, a data model for a generic event is included with multiple parameters as well as child events that inherit from this generic class. In various embodiments, the child events may be specialized. In various embodiments, the events may be broken up into categories, as shown in FIG. 3G. In various embodiments, not all events need rigorous time tracking, though some do and may display visual or generate audio indicators when the events are time sensitive. Some examples of time sensitive events include pulse check alerts (every 2 minutes), vasopressor administration (typically epinephrine, every 3-5 minutes), anti-arrhythmic administration, and CPR interruption timers. In various embodiments, simulation events may be included for training/teaching purposes.

In various embodiments, as shown in FIG. 3G and FIG. 3H, various attributes associated with each logged event may include algorithm, cpr, created, downtime, endTime, ph, phcycles, phlastepi, sim, simdowntime, simuptime, started, startTime, temporary, uid, uptime, and/or weight. Moreover, as shown in FIG. 3H, glucose (e.g., administered glucose solution, blood glucose level, etc.) may be logged. In various embodiments, the logged glucose, like the other logged data (e.g., LoggedAirway, LoggedShock, etc.), may feed into the LoggedEvent class.

Figure 4A:
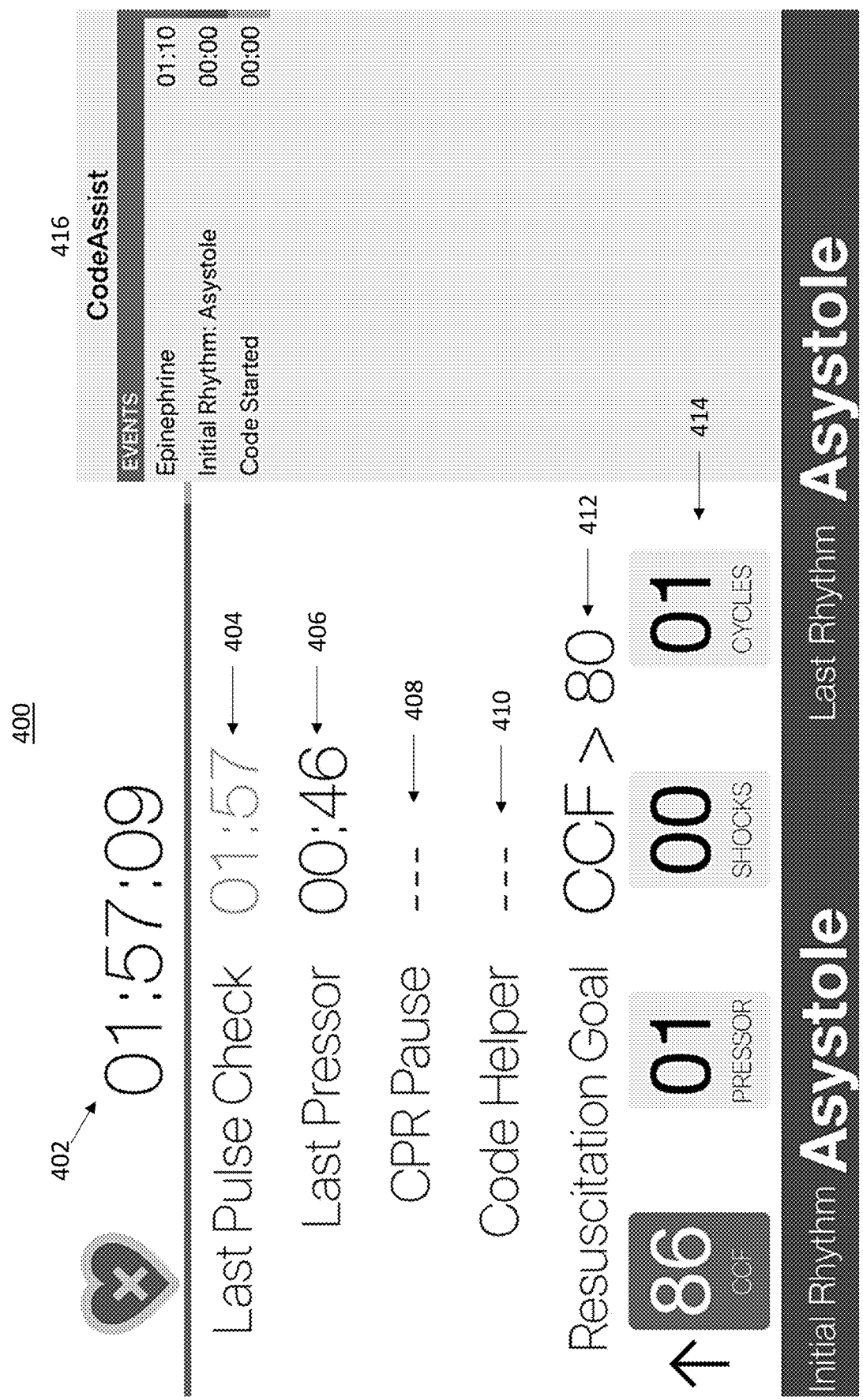
FIGS. 4A-4E illustrate various displays for tracking cardiac resuscitation events according to embodiments of the present disclosure.
Figure 4B:
Figure 4C:
Figure 4D:
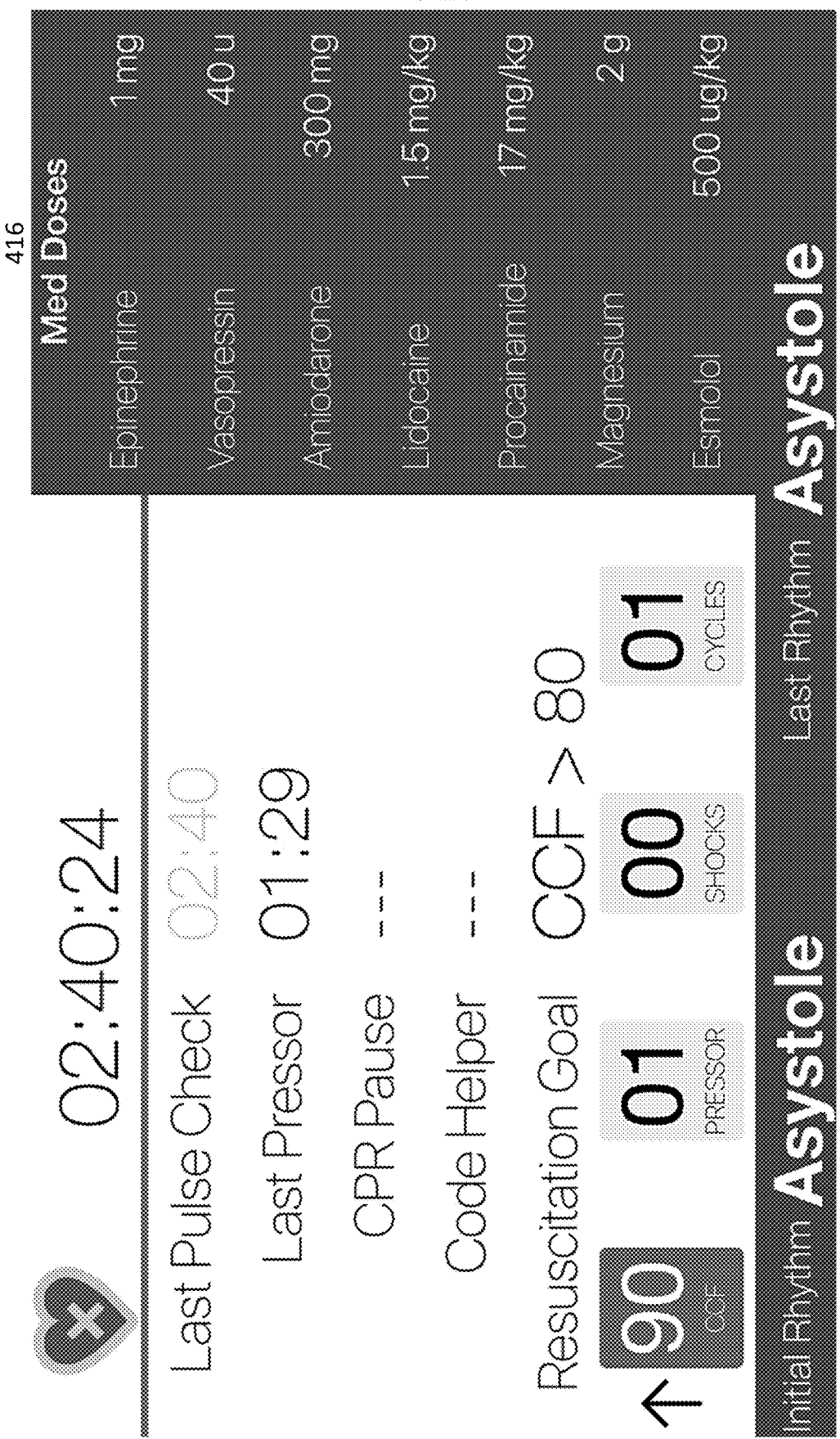

FIGS. 4A-4E illustrate various displays for tracking cardiac resuscitation events according to embodiments of the present disclosure. FIG. 4A shows an exemplary HUD 400 that may be displayed on an external display for broadcasting relevant information to a healthcare team performing a resuscitation. For example, the HUD includes a timer 402 for total elapsed time, a timer 404 for the last time a pulse was checked, a timer 406 for last pressor administration, a timer 408 for CPR pause, a timer 410 for code helper, an indication 412 of the resuscitation goal, and other information 414 such as chest compression fraction (CCF), number of pressors administered, number of shocks administered, and number of resuscitation cycles performed. In various embodiments, indications of initial and/or last heart rhythm may also be displayed (e.g., asystole). In various embodiments, the HUD 400 further includes a panel 416 displaying additional information that may be swapped out for other panels of information as shown in FIGS. 4B-4F. FIG. 4B shows a panel 416 including defibrillation information. FIG. 4C shows a panel 416 including the "H's and T's" of reversible causes. FIG. 4D includes a panel 416 including medication administration information. In various embodiments, the healthcare provider in charge of logging events (e.g., the provider having user privileges to access these features) may change the panel 416 depending on what information is relevant. In various embodiments, the system may automatically change the panel 416 to reflect relevant information based on where the healthcare providers are in the resuscitation procedure.

Figure 4E:

As shown in FIG. 4E, an alert is displayed over the screen indicating that a Long CPR pause has occurred. In various embodiments, predetermined alerts may be set to warn healthcare providers when certain thresholds are passed. For example, when the CPR pause timer passes a certain threshold (e.g., 30 seconds), an alert may pop up on the screen and/or a sound may be used to warn the healthcare providers performing the resuscitation. In another example, if the CCF drops below a predetermined threshold, an alert may pop up on the screen and/or a sound may be used to warn the healthcare providers performing the resuscitation. In various embodiments, the system may provide recommended courses of action (e.g., administration of a medication, defibrillation, chest compressions, etc.) if a threshold is passed thereby triggering an alert.

In various embodiments, the system may provide recommendations via the panel 416, such as recommended medications and/or doses. Recommended next steps in the resuscitation procedure may be recommended based on values such as the total elapsed time (and/or any other timer), CCF, number of administered medications, number of administered shocks, and/or cycles. In various embodiments, the system may use a cognitive system to provide the recommendations. In various embodiments, the cognitive system may be trained on data from previous resuscitations and/or data from the standard of care. In various embodiments, the cognitive system may include a neural network.

Figure 5A:
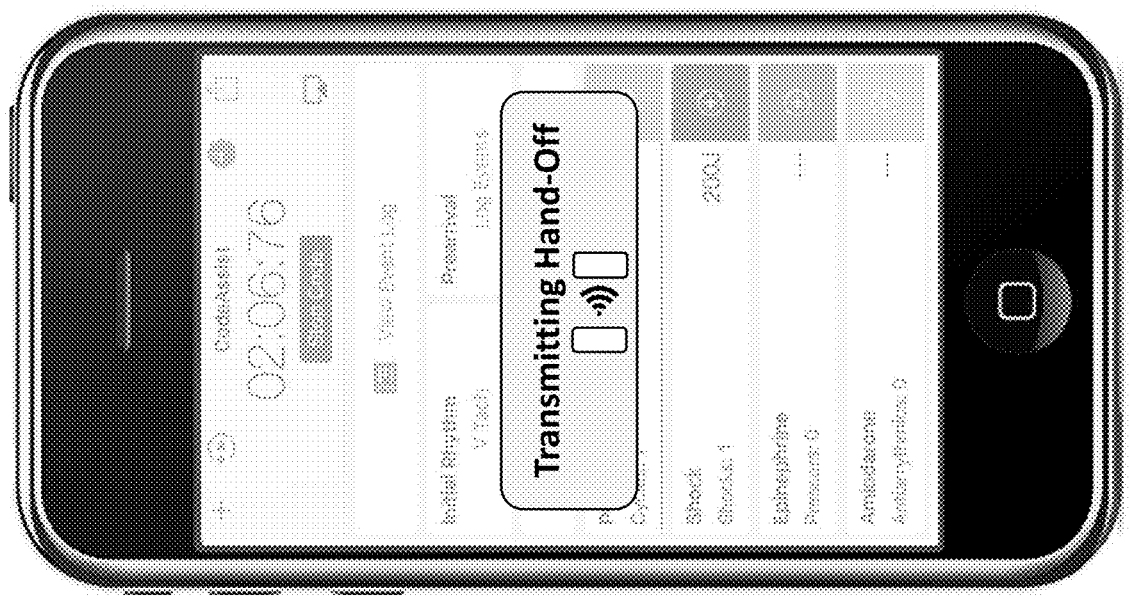
FIGS. 5A-5B illustrate mobile devices handing off a healthcare provider role according to embodiments of the present disclosure.
Figure 5B:
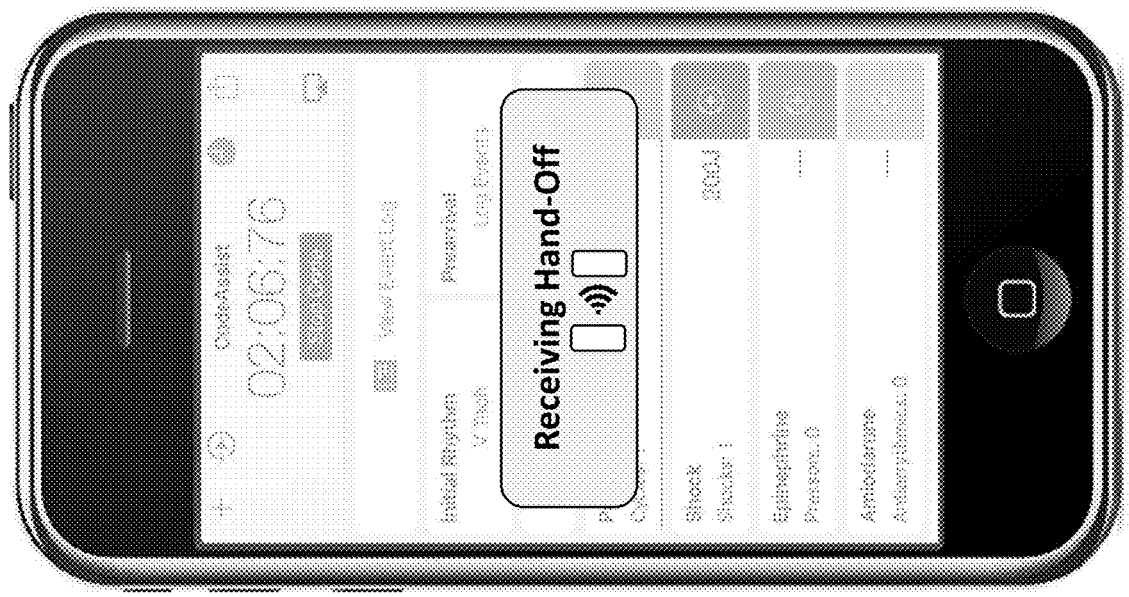

FIGS. 5A-5B illustrate mobile devices handing off a healthcare provider role according to embodiments of the present disclosure. As described above, in various situations, a healthcare provider that is responsible for logging the events and data during a resuscitation may be called to care for another emergency or pre-hospital care providers hand off the status of the resuscitations when transferring a patient to hospital care providers. In various embodiments, the handoff may be implemented as a mobile-to-mobile handoff using Bluetooth, Wi-Fi, near field communication (NFC), or any suitable communications protocol as is known in the art. In various embodiments, one mobile device may communicate with a remote server (e.g., a cloud server), which relays the required data and privileges to another mobile device. For example, one healthcare provider responsible for logging resuscitation events and patient data during the resuscitation may select a hand-off button and then select another healthcare provider to whom they will transfer the role of logging. In various embodiments, the system notifies the receiving healthcare provider that they are to receive a hand-off. In various embodiments, the receiving healthcare provider must provide an indication that they accept the hand-off by, for example, tapping an 'accept' button on a touch screen device. In various embodiments, the hand-off may be performed instantaneously based on distance and/or strength of signal. For example, if two device are brought within a predetermined distance of one another (e.g., within 2 inches) while the application is running, the handoff may be automatically performed to the other device.

In various embodiments, the hand-off transfers the current state of the application, including all patient data, event timer(s), logged resuscitation events, custom events, custom medications, and/or user privileges to control the external display (or HUD) that displays information to the healthcare team performing the resuscitation for seamless transition from one healthcare professional to another.

In various embodiments, the patient data may include demographics, patient attributes (e.g., height, weight, etc.), medications, allergies, and/or custom notes for the patient. In various embodiments, the patient data may be anonymized such that no revealing information about a particular patient is provided during a hand-off to another health care professional. For example, the system may anonymize any patient data (e.g., name, birthday, providing physician name) that could be used to identify the patient. In various embodiments, the system may not collect any data that may identify a patient. In various embodiments, the system anonymizes protected health information (PHI) of a patient according to the HIPAA standards. In various embodiments, protected health information includes all individually identifiable health information, including demographic data, medical histories, test results, insurance information, and other information used to identify a patient or provide healthcare services or healthcare coverage. 'Protected' means the information is protected under the HIPAA Privacy Rule.

In various embodiments, the system may utilize a universal clock to synchronize the event timer(s) between the first, transferring device and the second, receiving device such that no timer is stopped during the transfer (i.e., there is either no difference or negligible difference between a timer on the first transferring device and a corresponding timer on the second, receiving device). In various embodiments, the transferring device may send a time-stamped message with the time of the event timer(s) in addition to the universal clock time. In various embodiments, the receiving device receives the time-stamped message and, if necessary, adjusts the event timer(s) for any latency of the network by comparing the universal clock time in the message to the current universal clock time. For example, if the message was sent with a universal clock time stamp of 15:00:00 and one event timer at 4:23:00 and the receiving device received the message at a universal clock time of 15:00:02, then the receiving device would adjust the event timer to be 4:23:02.

In various embodiments, the system may utilize an ad hoc approach to synchronize the event timer(s) between the first, transferring device and the second, receiving device such that no timer is stopped during the transfer (i.e., there is either no difference or negligible difference between a timer on the first transferring device and a corresponding timer on the second, receiving device). In various embodiments, when a message having the event timer(s) is received at the receiving device, the receiving device may ping the transferring device one or more times to determine (e.g., approximate) a latency of the network. In various embodiments, the receiving device may adjust the received event timer(s) based on the determined latency of the network over which the transfer is occurring.

Figure 6:
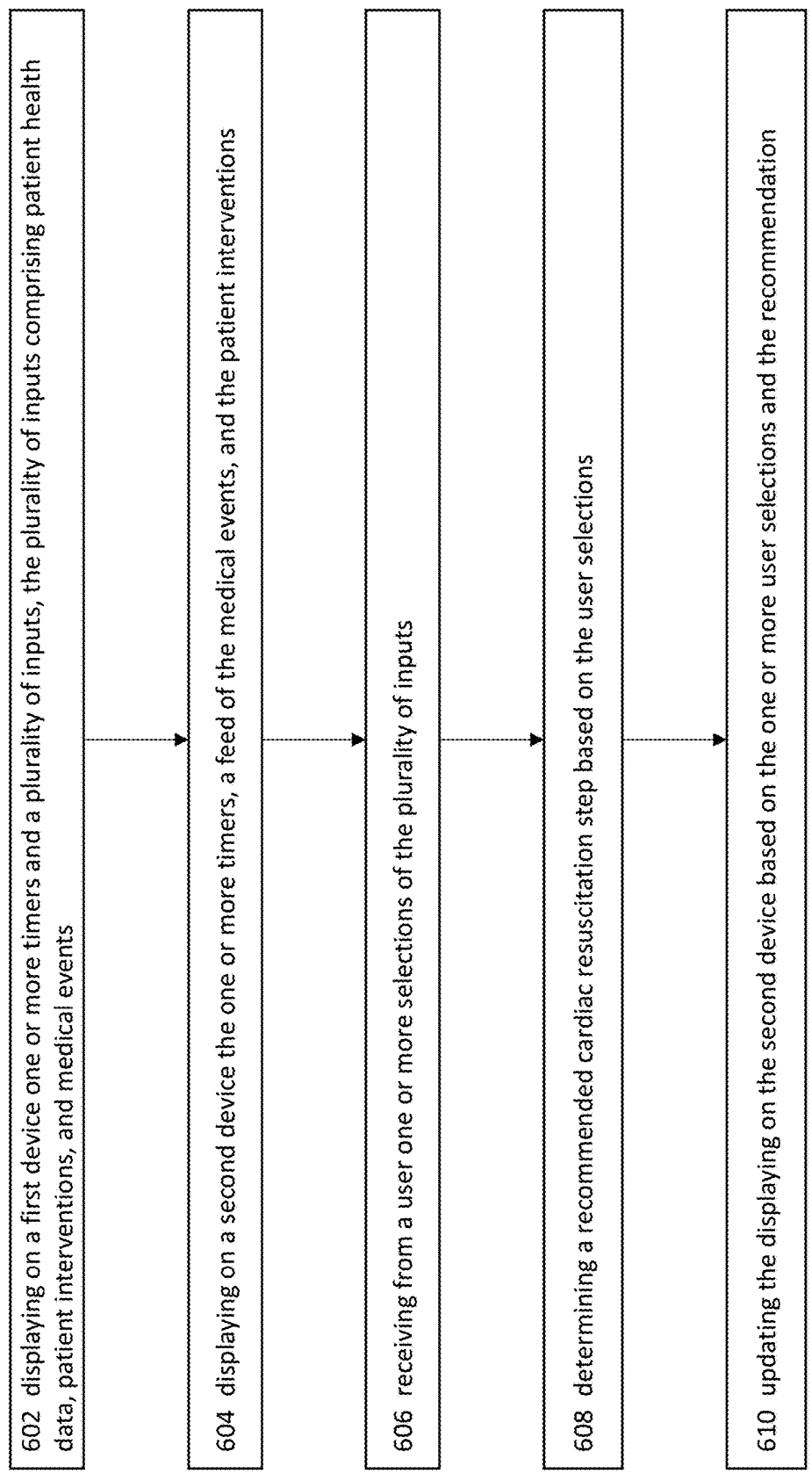
FIG. 6 illustrates a flowchart of a method for cardiac resuscitation timing according to embodiments of the present disclosure.

FIG. 6 illustrates a flowchart 600 of a method for cardiac resuscitation timing according to embodiments of the present disclosure. At 602, one or more timers and a plurality of inputs are displayed on a first device. The plurality of inputs include patient health data, patient interventions, and medical events. At 604, the one or more timers, a feed of the medical events, and the patient interventions are displayed on a second device. At 606, one or more selections of the plurality of inputs are received from a user. At 608, a recommended cardiac resuscitation step is determined based on the user selections. At 610, the display on the second device is updated based on the one or more user selections and the recommendation.

Figure 7:
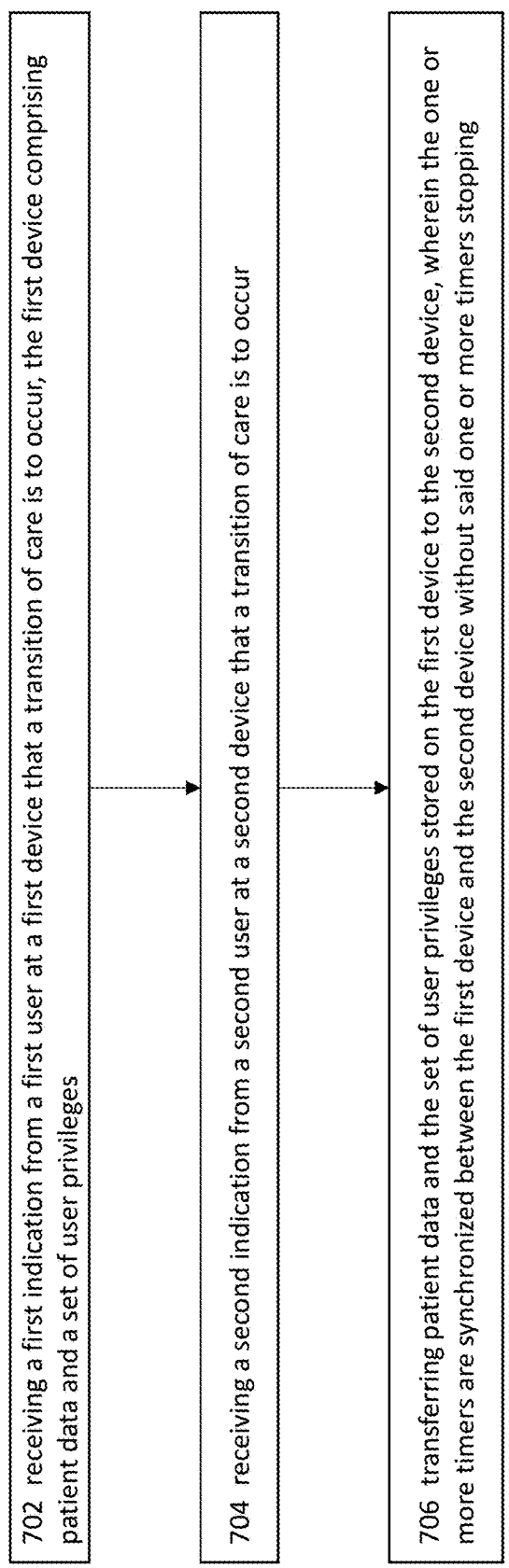
FIG. 7 illustrates a flowchart of a method for handing off a healthcare provider role during a transition of care according to embodiments of the present disclosure.

FIG. 7 illustrates a flowchart 700 of a method for handing off a healthcare provider role during a transition of care according to embodiments of the present disclosure. At 702, a first indication is received from a first user at a first device that a transition of care is to occur. The first device includes patient data, one or more timers, resuscitation event data, and a set of user privileges. At 704, a second indication is received from a second user at a second device that a transition of care is to occur. At 706, patient data and the set of user privileges stored on the first device are transferred to the second device. In various embodiments, the patient data and the set of user privileges may be removed from the first device upon completion of the transfer.

Figure 8:
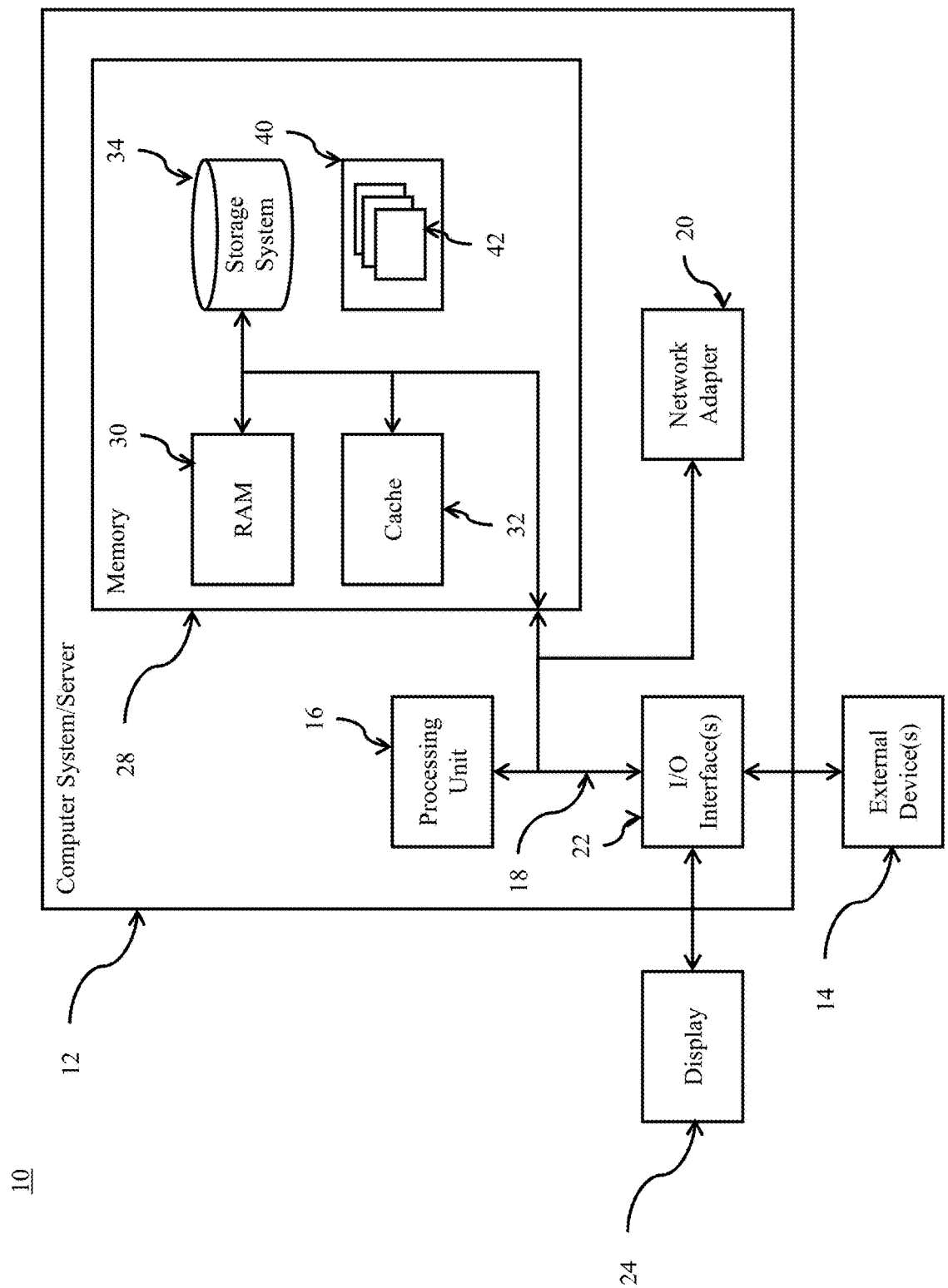
FIG. 8 depicts an exemplary computing node according to various embodiments of the present disclosure.

Referring now to FIG. 8, a schematic of an exemplary computing node is shown that may be used with the computer vision systems described herein. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 coupling various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In other embodiments, the computer system/server may be connected to one or more cameras (e.g., digital cameras, light-field cameras) or other imaging/sensing devices (e.g., infrared cameras or sensors).

The present disclosure includes a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

An electronic health record (EHR), or electronic medical record (EMR), may refer to the systematized collection of patient and population electronically-stored health information in a digital format. These records can be shared across different health care settings and may extend beyond the information available in a PACS discussed above. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information.

EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Health Level-7 or HL7 refers to a set of international standards for transfer of clinical and administrative data between software applications used by various healthcare providers. These standards focus on the application layer, which is layer 7 in the OSI model. Hospitals and other healthcare provider organizations may have many different computer systems used for everything from billing records to patient tracking. Ideally, all of these systems may communicate with each other when they receive new information or when they wish to retrieve information, but adoption of such approaches is not widespread. These data standards are meant to allow healthcare organizations to easily share clinical information. This ability to exchange information may help to minimize variability in medical care and the tendency for medical care to be geographically isolated.

In various systems, connections between a PACS, Electronic Medical Record (EMR), Hospital Information System (HIS), Radiology Information System (RIS), or report repository are provided. In this way, records and reports form the EMR may be ingested for analysis. For example, in addition to ingesting and storing HL7 orders and results messages, ADT messages may be used, or an EMR, RIS, or report repository may be queried directly via product specific mechanisms. Such mechanisms include Fast Health Interoperability Resources (FHIR) for relevant clinical information. Clinical data may also be obtained via receipt of various HL7 CDA documents such as a Continuity of Care Document (CCD). Various additional proprietary or site-customized query methods may also be employed in addition to the standard methods.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for handing off a healthcare provider role during a transition of care, the method comprising:
   receiving a first indication from a first user at a first device that a transition of care is to occur, the first device comprising patient data, one or more timers, resuscitation event data, and a set of user privileges;
   receiving a second indication from a second user at a second device that a transition of care is to occur;
   transferring patient data, one or more timers, resuscitation event data, and the set of user privileges stored on the first device to the second device, wherein the one or more timers are synchronized between the first device and the second device without said one or more timers stopping;
   continuing care for a patient based on the patient data, one or more timers and the resuscitation event data.

2. The method of claim 1, wherein the set of user privileges on the first device comprises access to a plurality of inputs and one or more timers.

3. The method of claim 2, wherein the plurality of inputs comprises patient health data, patient interventions, and medical events.

4. The method of claim 1, wherein the transferring is performed using near field communication.

5. The method of claim 1, further comprising removing the patient data and the set of user privileges from the first device after transferring.

6. The method of claim 1, wherein the transferring is performed using bluetooth.

7. The method of claim 1, wherein the transferring is performed over a network.

* * * * *